United States Patent
Okuda et al.

[11] Patent Number: 6,053,939
[45] Date of Patent: Apr. 25, 2000

[54] ARTIFICIAL BLOOD VESSEL

[75] Inventors: Yasuhiro Okuda; Fumihiro Hayashi, both of Osaka; Yutaka Okumura, Edogawa-ku, all of Japan

[73] Assignee: Vascular Graft Research Center Co., Ltd., Tokyo, Japan

[21] Appl. No.: 08/800,685

[22] Filed: Feb. 14, 1997

[30] Foreign Application Priority Data

| Feb. 15, 1996 | [JP] | Japan | 8-027823 |
| Feb. 15, 1996 | [JP] | Japan | 8-027824 |
| Feb. 15, 1996 | [JP] | Japan | 8-027825 |
| Feb. 15, 1996 | [JP] | Japan | 8-027829 |
| Mar. 29, 1996 | [JP] | Japan | 8-076293 |
| Jun. 14, 1996 | [JP] | Japan | 8-153868 |
| Jun. 14, 1996 | [JP] | Japan | 8-153880 |
| Jun. 14, 1996 | [JP] | Japan | 8-153883 |

[51] Int. Cl.$^7$ ................................................ A61F 2/06
[52] U.S. Cl. ................... 623/1; 623/11; 600/36; 600/37
[58] Field of Search ................... 623/1, 11; 600/37, 600/36

[56] References Cited

U.S. PATENT DOCUMENTS

| 4,193,138 | 3/1980 | Okita . | |
| 4,208,745 | 6/1980 | Okita | 3/1.4 |
| 4,613,517 | 9/1986 | Williams et al. . | |
| 4,822,361 | 4/1989 | Okita et al. . | |
| 5,019,393 | 5/1991 | Ito et al. | 424/423 |
| 5,028,597 | 7/1991 | Kodama et al. | 514/56 |
| 5,034,265 | 7/1991 | Hoffman et al. . | |
| 5,118,524 | 6/1992 | Thompson et al. | 427/2 |
| 5,217,492 | 6/1993 | Guire et al. | 623/1 |
| 5,591,225 | 1/1997 | Okuda | 623/1 |
| 5,665,114 | 9/1997 | Weadock et al. | 623/1 |

FOREIGN PATENT DOCUMENTS

| 2132033 | 9/1995 | Canada . |
| 0 246 638 | 11/1987 | European Pat. Off. . |
| 0 415 845 | 3/1991 | European Pat. Off. . |
| 0 481 160 | 4/1992 | European Pat. Off. . |
| 0 608 095 | 7/1994 | European Pat. Off. . |
| 59-200656 | 11/1984 | Japan . |
| 60-99259 | 6/1985 | Japan . |
| 62-152469 | 7/1987 | Japan . |
| 63-46169 | 2/1988 | Japan . |
| 3-280948 | 12/1991 | Japan . |
| 4-300537 | 10/1992 | Japan . |
| 5-269198 | 10/1993 | Japan . |
| 2 033 232 | 5/1980 | United Kingdom . |
| 84/01892 | 5/1984 | WIPO . |
| 90/05755 | 5/1990 | WIPO . |
| 91/17744 | 11/1991 | WIPO . |
| 92/17218 | 10/1992 | WIPO . |
| 93/05730 | 4/1993 | WIPO . |
| 93/18214 | 9/1993 | WIPO . |

OTHER PUBLICATIONS

Abstract of JP405269198A published Oct. 19, 1993.

(List continued on next page.)

*Primary Examiner*—Paul B. Prebilic
*Attorney, Agent, or Firm*—Pillsbury Madison & Sutro LLP

[57] ABSTRACT

An artificial blood vessel formed into a tube from expanded polytetrafluoroethylene (PTFE), wherein the tube is composed of nodes connected by fibrils creating pores within the wall of the tube. The inner surface of the tube and surfaces of pores comprise a layer extending radially from the inner surface, toward the outer surface of the tube to a depth of 5% to 96%, are chemically treated to make the tube inner surface and pores hydrophilic. Tissue-inducing substances and anti-thrombotic substances are then covalently bonded to the hydrophilic inner surface of the tube and pores. An artificial blood vessel of the invention exhibits a good patency ratio for a long period of time.

14 Claims, 2 Drawing Sheets

OTHER PUBLICATIONS

Costello et al, "Surface–Selective Introduction of Specific Functionalities onto Poly(tetrafluoroethylene)[1]", Macromolecules, vol. 20, No. 11, 1987, pp. 2819–2828.

Hegazy et al, "Radiation–Initiated Graft Copolymerization of Individual Monomer and Comonomer onto Polyethylene and Polytetrafluoroethylene Films", Journal of Applied Polymer Science, vol. 39, pp. 1029–1043.

Chapiro et al, "Synthesis of Permselective Membranes by Radiation Induced Grafting of Hydrophilic Monomers into Poly(Tetrafluoroethylene) Films", Polymer Engineering and Science, Feb. 1980, vol. 20, No. 3, pp. 202–205.

Morel et al, Structure and Morphology of Poly(Tetrafluoroethylene)–Poly(N–Vinylpyrrolidone) Copolymer Membranes, Journal of Applied Polymer Science, vol. 24, pp. 771–780.

Aiba et al, "Preparation of Poly(styrenesulfonic Acid)–Grafted Microporous Polytetrafluoroethylene Membranes and Their Activity as Hydrolysis Catalysts", Makromol. Chem., Rapid Commun. 7, pp. 91–96 (1986).

Tanfani et al, "Glycidyl Acrylate Plasma Glow Discharged Polymers", Biomaterials 1990, vol. 11, pp. 585–589.

Massia et al, "Human Endothelial Cell Interactions with Surface–Coupled Adhesion Peptides on a Nonadhesive Glass Substrate and Two Polymeric Biomaterials", Journal of Biomedical Materials Research, vol. 25, pp. 223–242.

Okada et al, "Evaluation of Collagen–Immobilized Percutaneous Implants", Polym. Mater. Sci. Eng., pp. 548–552 (1988).

Dekker et al, "Adhesion of Endothelial Cells and Adsorption of Serum Proteins on Gas Plasma–Treated Polytetrafluoroethylene", Biomaterials 1991, vol. 12, pp. 130–138.

Ramalanjaona et al, "The Effect of Fibronectin Coating on Endothelial Cell Kinetics in Polytetrafluoroethylene Grafts", J. Vascular Surgery, vol. 3, No. 2, (1986), pp. 264–272.

Seeger et al, "Improved in Vivo Endothelialization of Prosthetic Grafts by Surface Modification With Fibronectin", J. Vascular Surgery, vol. 3, No. 2, (1988), pp. 476–482.

Schneider et al, "Performed Confluent Endothelial Cell Monolayers Prevent Early Platelet Deposition on Vascular Prostheses in Baboons", Journal of Vascular.

Kesler et al, "Enhanced Strength of Endothelial Attachment on Polyester Elastomer and Polytetrafluoroethylene Graft Surfaces With Fibronectin Substrate", Journal of Vascular Surgery, vol. 3, No. 1, pp. 58–64 (1986).

Scott et al, "A Collagen Coated Vascular Prosthesis", Journal of Cardiovascular Surgery, vol. 28, 1987, pp. 498–504.

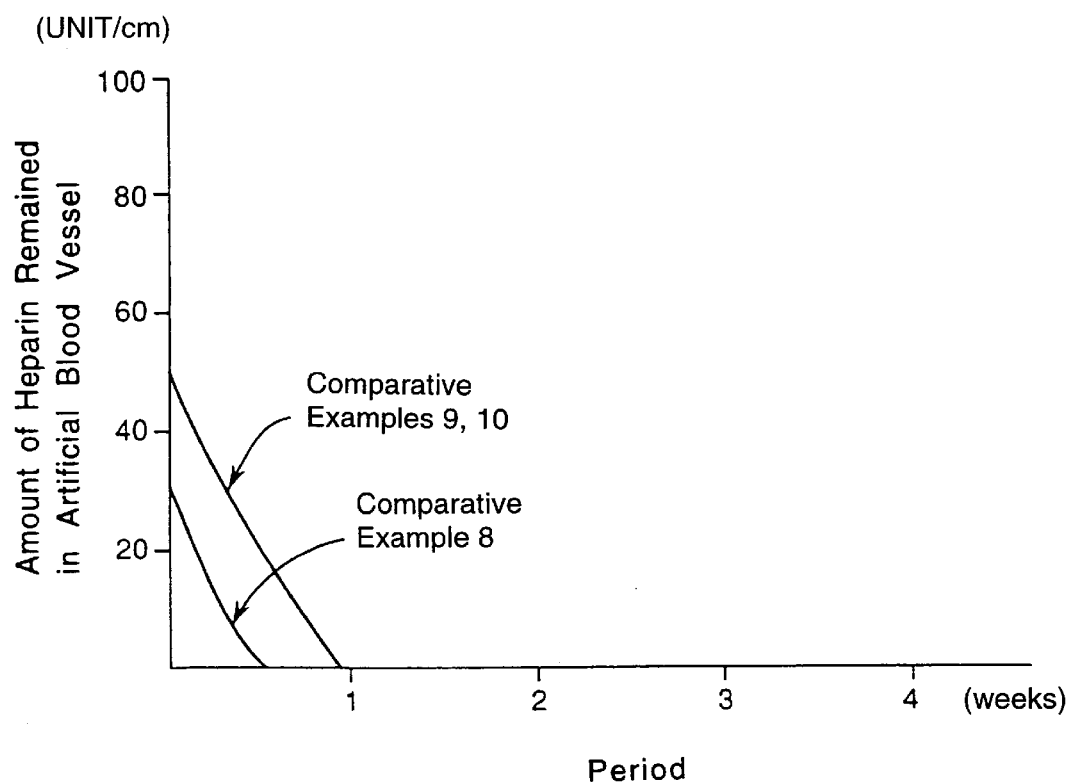

ARTIFICIAL BLOOD VESSEL

BACKGROUND OF THE INVENTION

1. Field of the Invention

The present invention relates to an artificial blood vessel. In particular, the present invention relates to an artificial blood vessel which is preferably used as a substitute blood vessel for replacing small-diameter blood vessels such as coronary arteries, peripheral blood vessels and the like.

2. Description of the Related Art

Tubes of woven or knitted fabric of polyester fibers and expanded polytetrafluoroethylene (hereinafter referred to as "EPTFE") are used as artificial blood vessels. The EPTFE tubes are practically used in a smaller diameter range rather than the polyester tubes since PTFE itself has excellent anti-thrombotic properties, and the pore structure of EPTFE tube comprising fibrils and nodes which is obtained by expanding PTFE tube has excellent biocompatibility.

However, EPTFE does not always have satisfactory anti-thrombotic properties, and the EPTFE tubes do not have a sufficient patency ratio when they have an inner diameter of 5 mm or less, in particular 4 mm or less. To remove this drawback of the EPTFE tube, the following methods have been proposed:

(1) improvement of anti-thrombotic properties of materials of artificial blood vessels;

(2) growing or seeding anti-thrombotic tissues on inner surfaces of artificial blood vessels; and (3) accelerating the formation of tissues on inner surfaces of artificial blood vessels after grafting the artificial blood vessels.

Concretely, as the method (1), developments of anti-thrombotic polymer materials having a microphase separation structure or anti-thrombotic agent-immobilized materials have been discussed (see Noishiki et al, Trans. A. S. A. I. O., 23, 253 (1977), JP-A-58-180162 and JP-A-63-119773). Such the anti-thrombotic materials can prevent the formation of thrombus temporarily after grafting, but thrombus forms and occludes the blood vessels after a long time from grafting.

As the method (2), a method for seeding vascular endothelial cells on the inner walls of artificial blood vessels has been proposed. However, the provision of human vascular endothelial cells is difficult, and the collection and culturing of such the cells require several weeks. Therefore, this method has not been used in practice (see Takagi et al, JINKOZOKI (Japanese Journal of Artificial Organs), 17, 679 (1988) and JP-A-1-170466).

As the method (3), artificial blood vessels on which endothelial cell-adhesion or growth materials are coated or covalently bonded have been proposed.

An artificial blood vessel is known, which sustainingly releases heparin for imparting anti-thrombotic properties to the blood vessel. For example, an artificial blood vessel to which heparin is immobilized using a material containing a quaternary ammonium salt or protamine has been proposed (see JP-A-58-180162 and JP-A-63-119773).

An artificial blood vessel on which the endothelial cell-adhesion material and optionally the endothelial cell-growth material are coated is proposed, but the formation of endothelial cells is not accelerated and the patency does not improve (C. H. Lundgren et al, Trans. A. S. A. I. O., 32, 346 (1986), and Glysler et al, SURGERY, 112, 244 (1992)).

An artificial blood vessel to which an endothelial cell-adhesion material is chemically immobilized is proposed (see JP-A-5-269198). In addition, an article reports that a material to which the endothelial cell-adhesion material and endothelial cell-growth material are both covalently bonded facilitated the formation of endothelial cells in vivo. However, an artificial blood vessel made of such the material loses its effects after grafting, and its patency is unsatisfactory (see J. Biomed. Mater. Res., 27, 901 (1993), etc.).

Furthermore, an artificial blood vessel which is coated with an endothelial cell-adhesion material such as collagen or gelatin and heparin has been proposed for suppressing the formation of thrombus prior to the formation of endothelial cells. However, neither the formation of endothelial cells nor the suppression of the thrombus formation is insufficient, and no satisfactory patency is achieved (see JP-A-63-46169).

A required amount of heparin must be released in a requisite period after grafting for achieving a high patency ratio. In particular, a required amount and requisite period for releasing heparin vary with the conditions of living bodies such as the blood flow and inner diameters of blood vessels to be replaced. Therefore, it is necessary to design a heparin-immobilized artificial blood vessel which satisfy the releasing amount and period of heparin according to respective artificial blood vessels.

However, it is difficult for the conventional heparin-immobilized artificial blood vessels to control the amount of immobilized heparin and the rate of sustained release of heparin since heparin is ionically bonded to the quaternary ammonium salt or protamine which has been coated on the surface of the artificial blood vessel. Therefore, it is difficult to sustainingly release heparin in a sufficient amount for maintaining the patency of artificial blood vessel in a requisite period, and the sufficient patency ratio is not attained.

SUMMARY OF THE INVENTION

An object of the present invention is to provide an artificial blood vessel which has a high patency ratio after grafting.

Another object of the present invention is to provide an artificial blood vessel which can facilitate the growth of endothelial cells while suppressing the formation of thrombus after grafting.

Accordingly, the present invention provides an artificial blood vessel comprising:

a tube formed from expanded polytetrafluoroethylene comprising fibrils and nodes connecting fibrils, in which the inner surface of said tube and the surfaces of pores in a layer portion extending from the inner surface of said tube to a depth of at least 5% in a radial direction from said inner surface are made hydrophilic, and a tissue-inducing substance which is immobilized on said inner surface and said surfaces of pores which are made hydrophilic.

In a preferred embodiment, the artificial blood vessel of the present invention further comprises an anti-thrombotic substance immobilized on at least a part of a surface of said tube which will be in contact with the blood in use.

The properties required for the artificial blood vessels vary with parts of living bodies in which the artificial blood vessels are implanted. On one hand, anti-thrombotic properties should be enhanced for the parts where a flow rate of blood is small such as peripheral blood vessels since thrombus tends to form in such the parts. Therefore, an anti-thrombotic substance is immobilized on the surfaces of the artificial blood vessels for preventing the formation of thrombus. On the other hand, the covering of the surfaces of the artificial blood vessels with the endothelial cells should be facilitated by immobilizing a tissue-inducing substance for the parts where a flow rate of blood is large since the formation of cell tissues is delayed while the thrombus is less formed.

BRIEF DESCRIPTION OF THE DRAWING

FIG. 2 is a graph showing the sustained release of heparin from the heparin-immobilized EPTFE artificial blood vessels used in Comparative Examples 8, 9 and 10.

DETAILED DESCRIPTION OF THE INVENTION

Figure 1:
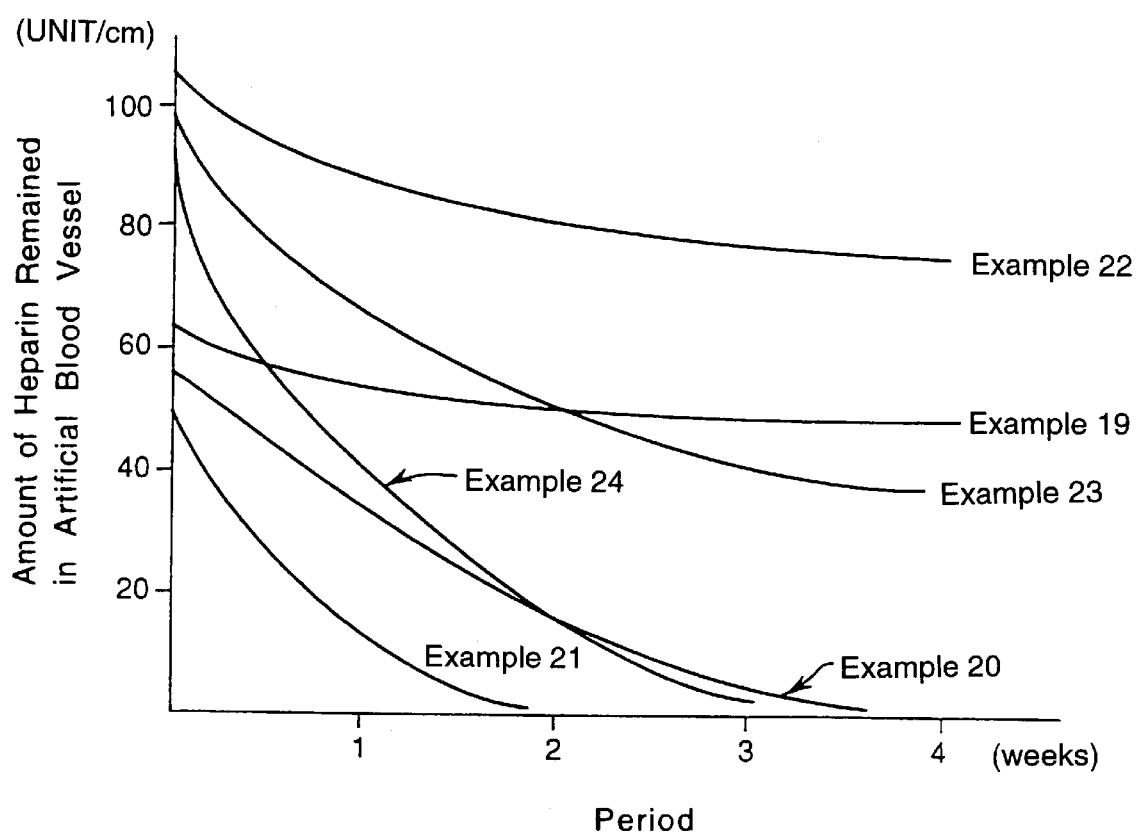
FIG. 1 is a graph showing the sustained release of heparin from the heparin-immobilized EPTFE artificial blood vessels prepared in Examples 19 through 24.

In general, the mean fibril length of EPTFE tube, that is, the mean length of the fibrils between nodes, is between 20 and 200 μm, the porosity of EPTFE tube is at least 50%, preferably at least 70%, and the wall thickness of the tube is between 300 and 1000 μm for adjusting the wall thickness of the artificial blood vessel to that of the living blood vessel.

The EPTFE tube preferably has a mean fibril length of at least 60 μm on a side of the tube which will be in contact with the blood in use. More preferably, the EPTFE tube has a multilayer structure having the mean fibril length of at least 60 μm on a side of the tube which will be in contact with the blood in use and at least one layer in which a fibril length of EPTFE tube is 40 μm or less.

When the EPTFE tube has the hydrophilic layer portion extending from its inner surface to the limited depth in the radial direction of the tube from the inner surface, hydrophilic groups can be chemically introduced into the tube wall by the following method:

Firstly, the porous wall of the EPTFE tube is masked to a certain depth from the outer surface of the tube with a material, which is not decomposed or denatured by the defluorination reaction, can be removed from the tube without damaging or denaturing the subsequently immobilized materials and has affinity to PTFE, such as paraffin, and the unmasked portion of the EPTFE tube is defluorinated by chemical treatment with alkali metal compounds, or by physical treatment such as irradiation with γ-ray or electron beams, corona discharge or glow discharge.

Then, functional groups are introduced in the unmasked portion by treating the defluorinated portion with compounds having carboxyl, hydroxyl, amino or epoxy groups.

Finally, the masking material is removed.

The patency ratio can be increased when a thickness of the wall which has not been masked is between 5% and 100%, preferably 5% and less than 96%, more preferably between 50% and 90%, of the wall thickness.
The wall which has not been masked is between 5% and 100%, preferably 5% and less than 96%, more preferably between 50% and 90%, of the wall thickness.

The wall thickness which is not masked can be adjusted by controlling a depth to which molten paraffin penetrates through the change of a temperature gradient in the tube wall by flowing a cooling medium such as water through the hole of the tube, or filling all the pores in the tube wall with paraffin and then extracting paraffin on the inner wall side.

When the tube wall is not masked, the entire wall is treated, and the functional groups are introduced onto all the surfaces of the pores which present in the tube wall as well as the inner and outer surfaces of the tube.

Among the defluorination methods, the chemical treatment with the alkali metals is more preferable than the physical treatment by irradiation with γ-ray or electron beams or corona or glow discharge.

The irradiation with γ-ray decomposes PTFE to deeper parts of the crystals of PTFE. Therefore the molecular weight of PTFE decreases and the strength of the EPTFE tube deteriorates greatly.

The glow discharge can treat only the outer and inner surfaces of the tube but may not treat surfaces of pores inside the tube wall, that is the surfaces of fibrils which constitute the pores in EPTFE.

The treatment with the alkali metal compounds can defluorinate the whole surfaces of the pores of EPTFE tube uniformly only to a depth of about several angstroms from the surfaces of fibrils and nodes constituting the pores, and does not decompose PTFE. Therefore, the strength of EPTFE tube does not decrease.

Since the inner and outer surfaces of the tube and also the surfaces of the pores inside the tube wall are defluorinated, proteins and peptides such as the tissue-inducing substances and anti-thrombotic substances can be covalently bonded to all of these surfaces.

Examples of the alkali metal compounds are methyllithium, n-butyllithium, tert.-butyllithium, sodium-naphthalene, sodium-benzophenone, vinyllithium and the like. They are used in the form of a solution. Among them, sodium-naphthalene and sodium-benzophenone will form a dark brown layer on the EPTFE surfaces after treatment and cannot treat EPTFE uniformly. Thus, methyllithium, n-butyllithium and tert.-butyllithium are preferable for the production of the artificial blood vessel of the present invention. Methyllithium, n-butyllithium and tert.-butyllithium should be used together with a chelating agent such as hexamethylphosphoric triamide or N,N,N',N'-tetramethylenediamine, since they have a weak activity for withdrawing the fluorine atom from EPTFE.

Examples of the compounds having the hydroxyl, carboxyl, epoxy or amino group are glycerol (meth)acrylate, 2-hydroxyethyl (meth)acrylate, 2-hydroxypropyl (meth)acrylate, polyethylene glycol (meth)acrylate, glycidyl (meth)acrylate, (meth)acrylic acid, allylamine, 2-aminoethyl (meth)acrylate, acrylamide and the like. Alternatively, an acid anhydride such as maleic anhydride is added and then hydrolyzed.

The tissue-inducing substance are immobilized onto the inner surface, pore surfaces and optionally outer surface of the EPTFE tube which have been made hydrophilic, by simply applying them or chemically bonding them to the already introduced functional groups. The anti-thrombotic substance is immobilized onto the surfaces which will be in contact with blood in use. The chemical bonding of the substances to the functional groups is preferable when the substances do not lose their activities by the chemical bonding. A method for immobilizing the substances is selected according to the kind of the already introduced functional groups, and preferably a method which does not inactivate the substances is selected.

For example, the substances are covalently bonded with the hydroxyl, carboxyl and amino groups through the dehydration-condensation, or with the epoxy group through the addition reaction. The substances are directly bonded with the hydroxyl group through the dehydration-condensation in the presence of carbodiimide as a catalyst. Alternatively, an eliminating group such as a trifluoromethanesulfonyl group is introduced into the hydroxyl group for improving the reactivity and then such the hydroxyl group is reacted with the amino group of the substances. The substances are directly bonded with the carboxyl group using a dehydration condensation catalyst such as carbodiimide. Alternatively, the carboxyl group is reacted with N-hydroxysuccinimide to introduce an active ester group in the carboxyl group and increase the reactivity and then the activated ester group is reacted with the amino group of the substances.

In particular, esters such as N-hydroxysuccinimide esters of carboxylic acids and sulfonate esters such as trifluoroethanesulfonate ester of the hydroxyl group are preferable as the functional groups for immobilizing the tissue-inducing substance by the covalent bond. That is, the tissue-inducing substance is reacted with these functional groups which have been formed by graft polymerization using the alkali metal compound. Then, the tissue-inducing moiety is covalently bonded with these functional groups by replacing the ester moiety or sulfonate ester moiety with the tissue-inducing moiety of the tissue-inducing substance. Thereby, the tissue-inducing effect after the grafting of the artificial blood vessel is improved, and the high patency ratio is obtained.

The method for immobilizing the tissue-inducing substance through the covalent bond after introducing the carboxylic acid group and converting it to the N-hydroxysuccinimide ester will be explained more in detail.

An EPTFE tube is dipped in a solution of an alkali metal compound such as methyllithium in, for example, diethyl ether under a nitrogen or argon atmosphere and hexamethylphosphoric triamide is added to the solution. Then, the solution containing the tube is kept standing at least 30 minutes at 0° C. or lower (e.g. −10° C.) to withdraw fluorine atoms from PTFE. After removing the solution, a solution of (meth)acrylic acid in an solvent such as tetrahydrofuran or water is added and reacted at an elevated temperature, for example, between 60° C. and 80° C. for at least 10 hours. After the reaction, excessive (meth)acrylic acid and non-grafted poly(meth)acrylic acid are washed off to obtain the grafted polymer of (meth)acrylic acid.

Then, the EPTFE tube on which poly(meth)acrylic acid has been grafted is dipped in a solution of N-hydroxysuccinimide and dicyclohexylcarbodiimide in a solvent such as 1,4-dioxane at 0° or lower for at least 12 hours to form N-hydroxysuccinimide ester.

After that, the EPTFE tube is dipped in a solution of the tissue-inducing substance in a phosphate buffer pH of which solution is adjusted to 11 to covalently bond the tissue-inducing substance.

Preferable examples of the tissue-inducing substance are cell-adhesion materials and cell-growth materials, since these materials achieve the best tissue-inducing functions. They may be used independently or in combination.

Examples of the cell-adhesion materials are collagen, gelatin, laminin, fibronectin and the like. Among them, fibronectin is preferable.

Examples of the cell-growth materials are TGF-α, transferrin, insulin, ECGF (endothelial cell growth factor), BPE (bovine pituitary extract), PDGF (platelet-derived growth factor), FGF (fibroblast growth factor) and the like. Among them, TGF-α, transferrin, insulin and FGF are preferable.

Examples of the anti-thrombotic substances are anti-coagulants (e.g. hirudin, heparin, etc.), plasminogen activators (e.g. t-PA, urokinase, etc.), fibrinolytic enzymes (e.g. plasmin, subtilisin, etc.), anti-platelet-aggregation agents (e.g. prostacyclin, aspirin, etc.) and the like.

The immobilized amount of the tissue-inducing substance is usually between 50 and 500 μg, preferably between 100 and 250 μg per 1 cm of the tube.

The immobilized amount of the anti-thrombotic substance is usually between 300 and 2000 μg, or between 60 and 400 units for heparin, preferably between 400 and 750 μg or between 80 and 150 units for heparin, per 1 cm of the tube.

In a preferred embodiment, the anti-thrombotic substance is ionically immobilized onto a polyamine or its salt which is covalently bonded to EPTFE tube through a polymer which has been graft polymerized, on the surface of the tube which will be in contact with the blood in use. Such the ionic immobilization of the anti-thrombotic substance enables sustained release of the anti-thrombotic substance, and achieves the high patency ratio.

The polyamine herein used is intended to mean a synthetic polymer comprising amino groups as repeating units. Preferable examples of the polyamine are polyallylamine, polyvinylamine, polyethyleneimine and their salts, and also mixtures of these polymers and/or salts.

In a preferable case, the amino groups of the polyamine are partially acetylated. Preferably up to 90%, more preferably 20 to 70% of the amino groups are acetylated. The acetylation of the amino groups controls the sustained release rate of the anti-thrombotic substance such as heparin. That is, the sustained release rate depends on the degree of acetylation of the amino groups. When the degree of acetylation is higher, the anti-thrombotic substance is released in an earlier stage, while the degree of acetylation is lower, the anti-thrombotic substance is released over a longer period. As the result, the adjustment of the degree of acetylation enables the artificial blood vessels to release the necessary amount of the anti-thrombotic substance in the blood over the required period, and maintains the patency of the artificial blood vessel over a long period.

The polyamine can be covalently bonded to the surface of the EPTFE tube by reacting the amino group of the polyamine with functional groups (e.g. carboxyl, aldehyde, hydroxyl groups, etc.) which have been introduced on the surface of the EPTFE tube and can covalently bond with the amino groups of the polymer. Such the functional groups can be introduced in the analogous methods to those explained above.

An example of the method for covalently bonding the polyamine to the functional group formed on the EPTFE surfaces will be explained using the carboxyl group as the functional group by way of example:

On the surfaces of the EPTFE tube, (meth)acrylic acid is graft polymerized by the same method as described above.

Then, the amino group of the polyamine is covalently bonded with the carboxyl group through the dehydration-condensation. The dehydration reaction may be performed using a carbodiimide such as 1-ethyl-3-(dimethylaminopropyl)carbodiimide. Alternatively, the carboxyl group is converted to an ester group such as the N-hydroxysuccinimide ester to increase the reactivity, and then reacted with the polyamine.

The amino groups of the polyamine may be acetylated prior to or after the covalent bonding of the polyamine to the surface of the EPTFE tube.

The acetylation can be performed by any known method, for example, by reacting the polyamine with acetic acid in the presence of 1-ethyl-3-(dimethylaminopropyl)-carbodiimide. The degree of acetylation can be controlled by adjusting the acetylation time.

The molecular weight of the polyamine is usually between 1000 and 100,000 in terms of a weight average molecular weight which is measured on a 3.5 M solution of the polyamine in saline by the sedimentation equilibrium method. When the molecular weight is less than 1000, the amount of the immobilized anti-thrombotic substance tends to decrease. When the molecular weight exceeds 100,000, the efficiency for immobilizing the anti-thrombotic substance to EPTFE tube tends to decrease.

The anti-thrombotic substance is ionically immobilized to the surfaces of the EPTFE tube by dipping the EPTFE tube carrying the covalently bonded polyamine in the solution of the anti-thrombotic substance.

In another embodiment, the anti-thrombotic substance may be immobilized only to the nodes of EPTFE on the surface of the tube which will be in contact with the blood in use. To this end, the EPTFE tube preferably has a mean distance between nodes, that is, a mean fibril length of at least 60 $\mu$m on a side of the tube which will be in contact with the blood in use. More preferably, the EPTFE tube has a multilayer structure having the mean fibril length of at least 60 $\mu$m on a side of the tube which will be in contact with the blood in use and at least one layer in which a fibril length of EPTFE tube is between 20 and 40 $\mu$m.

The mean fibril length means an average distance between the nodes which connect the fibrils of the EPTFE tube and is measured using a scanning electron microscope (SEM). That is, the fibril lengths are measured in three fields of view at thirty points in each field of view in the SEM photograph and averaged.

The artificial blood vessel in which the tissue-inducing substance is immobilized onto all the surfaces of the EPTFE tube including the pore surfaces, and the anti-thrombotic substance is immobilized onto the inner surface of the tube can be produced by one of the following methods:

In the first method, only the tissue-inducing substance is immobilized onto all the surface of the first EPTFE tube, while the tissue-inducing substance and the anti-thrombotic substance are immobilized onto all the surfaces of the second EPTFE tube. Then, the first EPTFE tube is laminated over the outer surface of the second EPTFE tube.

In the second method, methacrylic acid is graft polymerized on all the surfaces of the EPTFE tube. Prior to the bonding of polyamine or its salt, all the portions of the EPTFE tube except the inner surface are masked with a masking material such as paraffin. Then, the polyamine or its salt is bonded to the unmasked inner surface, and the masking material is removed. Finally, the tissue-inducing substance and the anti-thrombotic substance are bonded. Thus, the anti-thrombotic substance is immobilized only onto the inner surface of the EPTFE tube to which the polyamine or its salt has been bonded, while the tissue-inducing substrate is immobilized onto all the surfaces of the EPTFE tube.

Preferably, the nodes exposed on the inner surface of the EPTFE tube which will be in contact with the blood occupies 5 to 50% of the whole inner surface area to effectively attain both of the anti-thrombotic and tissue-inducing effects.

The anti-thrombotic substance can be immobilized to the nodes of the inner surface of EPTFE tube as follows:

The EPTFE tube to which the tissue-inducing substance has been immobilized as explained above is compressed in the longitudinal direction, that is, the direction along the axis of the tube, and the fibrils of EPTFE tube are warped. By this warping of the fibrils, the nodes project from the inner surface of the tube. Under such condition of the tube, a solution of the anti-thrombotic substance is passed through the inside of the tube, and the anti-thrombotic substance is immobilized only on the nodes. After that, the tube is relaxed.

EXAMPLES

The present invention will be explained further in detail by the following Examples, in which a fibril length means a mean fibril length measured using a scanning electron microscope.

Example 1

Each of an EPTFE tube having an inner diameter of 2 mm, an outer diameter of 2.5 mm and a fibril length of 60 $\mu$m (Tube 1) and an EPTFE tube having an inner diameter of 2.5 mm, an outer diameter of 3 mm and a fibril length of 30 $\mu$m (Tube 2) was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amounts of acrylic acid were about 80 $\mu$g and about 120 $\mu$g per 1 cm of the tube for Tubes 1 and 2, respectively, when calculated from the weight change of the tubes.

Each tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The ungrafted polymer of meth of fibronectin were about 45 $\mu$g and about 70 $\mu$g per 1 cm of the tube for Tubes 1 and 2, respectively when calculated from the weight change.

Next, the tube was dipped in a solution of transferrin in a phosphate buffer (pH of 11) (100 ml), and transferrin was immobilized through the covalent bond. The immobilized amount of transferrin was about 35 $\mu$g and about 60 $\mu$g per 1 cm of the tube for Tubes 1 and 2, respectively when calculated from the weight change.

Then, Tube 1 was dipped in a 0.05% aqueous solution of heparin (available from SANOFI) for 10 minutes and freeze dried, and the heparin-immobilized EPTFE tube was obtained. The immobilized amount of heparin was about 200 $\mu$g per 1 cm of the tube when calculated from the weight change.

Finally, a stainless steel rod having a diameter of 2 mm was inserted in Tube 1. Then, Tube 2 was laminated over Tube 1 with close contact, and an artificial blood vessel was obtained.

Example 2

Each of an EPTFE tube having an inner diameter of 2 mm, an outer diameter of 2.5 mm and a fibril length of 60 $\mu$m (Tube 1) and an EPTFE tube having an inner diameter of 2.5 mm, an outer diameter of 3 mm and a fibril length of 30 $\mu$m (Tube 2) was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amounts of acrylic acid were about 80 $\mu$g and about 120 $\mu$g per 1 cm of the tube for Tubes 1 and 2, respectively when calculated from the weight change of the tubes.

Each tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 45 μg and about 70 μg per 1 cm of the tube for Tubes 1 and 2, respectively when calculated from the weight change.

Then, Tube 1 was dipped in a 0.05% aqueous solution of heparin (available from SANOFI) for 10 minutes and freeze dried, and the heparin-immobilized EPTFE tube was obtained. The immobilized amount of heparin was about 200 μg per 1 cm of the tube when calculated from the weight change.

Finally, a stainless steel rod having a diameter of 2 mm was inserted in Tube 1. Then, Tube 2 was laminated over Tube 1 with close contact, and an artificial blood vessel was obtained.

Example 3

A stainless steel rod having a diameter of 2 mm was inserted in an EPTFE tube having an inner diameter of 2 mm, an outer diameter of 2.5 mm and a fibril length of 60 μm (Tube 1). Then, an EPTFE tube having an inner diameter of 2.5 mm, an outer diameter of 3 mm and a fibril length of 30 μm (Tube 2) was laminated over Tube 1 with close contact and heated at 340° C. for 20 minutes to adhere the tubes, and a laminated tube was obtained.

The laminated tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 190 μg per 1 cm of the tube when calculated from the weight change of the tube.

The tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 110 μg per 1 cm of the tube when calculated from the weight change.

Example 4

A stainless steel rod having a diameter of 2 mm was inserted in an EPTFE tube having an inner diameter of 2 mm, an outer diameter of 2.5 mm and a fibril length of 60 μm (Tube 1). Then, an EPTFE tube having an inner diameter of 2.5 mm, an outer diameter of 3 mm and a fibril length of 30 μm (Tube 2) was laminated over Tube 1 with close contact and heated at 340° C. for 20 minutes to adhere the tubes, and a laminated tube was obtained.

The laminated tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 190 μg per 1 cm of the tube when calculated from the weight change of the tube.

The tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of transferrin (30 mg) in a phosphate buffer (pH of 11) (100 ml), and transferrin was immobilized through the covalent bond to the ester groups. The immobilized amount of transferrin was about 93 μg per 1 cm of the tube when calculated from the weight change.

Example 5

A stainless steel rod having a diameter of 2 mm was inserted in an EPTFE tube having an inner diameter of 2 mm, an outer diameter of 2.5 mm and a fibril length of 60 μm (Tube 1). Then, an EPTFE tube having an inner diameter of 2.5 mm, an outer diameter of 3 mm and a fibril length of 30 μm (Tube 2) was laminated over Tube 1 with close contact and heated at 340° C. for 20 minutes to adhere the tubes, and a laminated tube was obtained.

The laminated tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 190 μg per 1 cm of the tube when calculated from the weight change of the tube.

The tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 110 μg per 1 cm of the tube when calculated from the weight change.

Then, the tube was dipped in a solution of transferrin (30 mg) in a phosphate buffer (pH of 11) (100 ml), and transferrin was immobilized through the covalent bond to the ester groups. The immobilized amount of transferrin was about 93 μg per 1 cm of the tube when calculated from the weight change.

Example 6

A stainless steel rod having a diameter of 2 mm was inserted in an EPTFE tube having an inner diameter of 2 mm, an outer diameter of 2.5 mm and a fibril length of 60 μm (Tube 1). Then, an EPTFE tube having an inner diameter of 2.5 mm, an outer diameter of 3 mm and a fibril length of 30 μm (Tube 2) was laminated over Tube 1 with close contact and heated at 340° C. for 20 minutes to adhere the tubes, and a laminated tube was obtained.

The laminated tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 190 μg per 1 cm of the tube when calculated from the weight change of the tube.

The tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 110 μg per 1 cm of the tube when calculated from the weight change.

Finally, the tube was dipped in a 0.02% aqueous solution of heparin (available from SANOFI) for 10 minutes and freeze dried, and the heparin-immobilized EPTFE tube was obtained. The immobilized amount of heparin was about 200 μg 1 cm of the tube when calculated from the weight change.

Example 7

An EPTFE tube having an inner diameter of 2 mm, an outer diameter of 3 mm and a fibril length of 60 μm was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 120 μg per 1 cm of the tube when calculated from the weight change of the tube.

The tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 90 μg per 1 cm of the tube when calculated from the weight change.

Example 8

Each of an EPTFE tube having an inner diameter of 2 mm, an outer diameter of 2.5 mm and a fibril length of 60 μm (Tube 1) and an EPTFE tube having an inner diameter of 2.5 mm, an outer diameter of 3 mm and a fibril length of 60 μm (Tube 2) was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amounts of acrylic acid were about 80 μg and about 90 μg per 1 cm of the tube for Tubes 1 and 2, respectively when calculated from the weight change of the tubes.

Each of the acrylic acid-grafted EPTFE tubes was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 45 μg and about 50 μg per 1 cm of the tube for Tubes 1 and 2, respectively when calculated from the weight change.

The tube 1 was dipped in a 0.05% aqueous solution of heparin (available from SANOFI) for 10 minutes and freeze dried, and the heparin-immobilized EPTFE tube was obtained. The immobilized amount of heparin was about 200 μg per 1 cm of the tube when calculated from the weight change.

Finally, a stainless steel rod having a diameter of 2 mm was inserted in Tube 1. Then, Tube 2 was laminated over Tube 1 with close contact, and an artificial blood vessel was obtained.

Example 9

Each of an EPTFE tube having an inner diameter of 2 mm, an outer diameter of 2.5 mm and a fibril length of 30 μm (Tube 1) and an EPTFE tube having an inner diameter of 2.5 mm, an outer diameter of 3 mm and a fibril length of 30 μm (Tube 2) was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amounts of acrylic acid were about 100 μg and about 120 μg per 1 cm of the tube for Tubes 1 and 2, respectively when calculated from the weight change of the tubes.

Then, each of the acrylic acid-grafted EPTFE tubes was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 50 μg and about 70 μg per 1 cm of the tube for Tubes 1 and 2, respectively when calculated from the weight change.

The tube 1 was dipped in a 0.05% aqueous solution of heparin (available from SANOFI) for 10 minutes and freeze dried, and the heparin-immobilized EPTFE tube was obtained. The immobilized amount of heparin was about 200 μg per 1 cm of the tube when calculated from the weight change.

Finally, a stainless steel rod having a diameter of 2 mm was inserted in Tube 1. Then, Tube 2 was laminated over Tube 1 with close contact, and an artificial blood vessel was obtained.

Comparative Example 1

An EPTFE tube having an inner diameter of 2 mm, an outer diameter of 3 mm and a fibril length of 30 μm was used as an artificial blood vessel.

Comparative Example 2

An EPTFE tube having an inner diameter of 2 mm, an outer diameter of 3 mm and a fibril length of 60 μm was used as an artificial blood vessel.

Comparative Example 3

An EPTFE tube having an inner diameter of 2 mm, an outer diameter of 2.5 mm and a fibril length of 60 μm (Tube 1) and an EPTFE tube having an inner diameter of 2.5 mm, an outer diameter of 3 mm and a fibril length of 30 μm (Tube 2) were provided.

A stainless steel rod having a diameter of 2 mm was inserted in Tube 1. Then, Tube 2 was laminated over Tube 1 with close contact and heated at 340° C. for 20 minutes to adhere two tubes.

Example 10

An EPTFE tube having an inner diameter of 2 mm, an outer diameter of 3 mm and a fibril length of 30 μm was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 210 μg per 1 cm of the tube when calculated from the weight change of the tubes.

The tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester. The esterified tube was dipped in a solution of fibronectin (30 mg) in a phosphate buffer (pH of 11) (100 ml), and fibronectin was immobilized through the covalent bond to the ester groups. The immobilized amount of fibronectin was about 110 μg per 1 cm of the tube when calculated from the weight change.

Example 11

A stainless steel rod having a diameter of 2 mm was inserted in an EPTFE tube having an inner diameter of 2 mm, an outer diameter of 2.5 mm and a fibril length of 60 μm (Tube 1). Then, an EPTFE tube having an inner diameter of 2.5 mm, an outer diameter of 3 mm and a fibril length of 30 μm (Tube 2) was laminated over Tube 1 with close contact and heated at 340° C. for 20 minutes to adhere the tubes, and a laminated tube was obtained.

The laminated tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 190 μg per 1 cm of the tube when calculated from the weight change of the tube.

Then, the tube was dipped in an aqueous solution containing 0.05% of fibronectin (derived from bovine plasma, manufactured by NIPPON HAM) and 0.5% of 1-ethyl-3-(3-dimethylaminopropyl)carbodiimide, pH of which had been adjusted to 5 with 1N hydrochloric acid, for 24 hours, removed from the solution and washed with water, and the fibronectin-immobilized EPTFE tube was obtained. The immobilized amount of fibronectin was about 110 μg per 1 cm of the tube.

Finally, the tube was dipped in an aqueous solution containing 0.05% of transferrin and 0.5% of 1-ethyl-3-(3-dimethylaminopropyl)carbodiimide, pH of which had been adjusted to 5 with 1N hydrochloric acid, for 24 hours, removed from the solution and washed with water, and the transferrin-immobilized EPTFE tube was obtained. The immobilized amount of transferrin was about 95 μg per 1 cm of the tube.

Ten artificial blood vessels (each having a length of 3 cm) prepared in each of Examples 1 to 11 and Comparative Examples 1 to 3 were implanted in carotid arteries of ten rabbits. The results are shown in Table 1.

The patency ratio means a ratio of the number of artificial blood vessels which maintained the blood flow after the specified time to the number of tested artificial blood vessels (ten blood vessels).

The artificial blood vessels which had the fibril length of 60 μm on the surface which is in contact with blood and the fibril length of 30 μ in other parts, and to which both fibronectin and heparin were immobilized had excellent patency ratios. In particular, those having heparin immobilized in the inner layer had the patency ratio of 100% (10/10).

The surface area which was covered with endothelial cells was measured with each artificial blood vessel. The artificial blood vessels to which fibronectin and/or transferrin were immobilized using N-hydroxysuccinimide (active ester method) had the high covered surface area. In particular, the artificial blood vessels to which both fibronectin and transferrin were immobilized had the highest covered surface area.

Many of the artificial blood vessels which did not contain the layer having the fibril length of 30 μm were warped after implantation and/or adhered to surrounding tissues heavily.

TABLE 1

| Ex. No. | Fibril length in inner layer/ outer layer (μm/μm) | Heparin- immobilized layer and amount (μg/cm) | Immobi- lization method[1] | Fibro- nectin (μg/cm) | Trans- ferrin (μg/cm) | Patency ratio (%) after One week | Patency ratio (%) after One month | Covering ratio (%) of endothelial cells after one month |
|---|---|---|---|---|---|---|---|---|
| Ex. 1 | 60/30 | Inner layer, 200 | A | 115 | 95 | 10/10 (100) | 10/10 (100) | 65 |
| Ex. 2 | 60/30 | Inner layer, 200 | A | 115 | 0 | 10/10 (100) | 10/10 (100) | 50 |
| Ex. 3 | 60/30 | 0 | A | 110 | 0 | 8/10 (80) | 8/10 (80) | 53 |
| Ex. 4 | 60/30 | 0 | A | 0 | 93 | 8/10 (80) | 7/10 (70) | 52 |
| Ex. 5 | 60/30 | 0 | A | 110 | 93 | 8/10 (80) | 8/10 (80) | 74 |
| Ex. 6 | 60/30 | All layers, 200 | A | 110 | 0 | 9/10 (90) | 7/10 (70) | 42 |
| Ex. 7 | 60/60 | 0 | A | 90 | 0 | 7/10 (70) | 7/10 (70) | 55 |
| Ex. 8 | 60/60 | Inner layer, 200 | A | 95 | 0 | 8/10 (80) | 7/10 (70) | 48 |

TABLE 1-continued

| Ex. No. | Fibril length in inner layer/ outer layer (μm/μm) | Heparin-immobilized layer and amount (μg/cm) | Immobilization method[1] | Fibronectin (μg/cm) | Transferrin (μg/cm) | Patency ratio (%) after One week | One month | Covering ratio (%) of endothelial cells after one month |
|---|---|---|---|---|---|---|---|---|
| Ex. 9 | 30/30 | Inner layer, 200 | A | 120 | 0 | 7/10 (70) | 6/10 (60) | 33 |
| C. Ex. 1 | 30/30 | 0 | | 0 | 0 | 5/10 (50) | 3/10 (30) | 30 |
| C. Ex. 2 | 60/60 | 0 | | 0 | 0 | 4/10 (40) | 4/10 (40) | 43 |
| C. Ex. 3 | 60/30 | 0 | | 0 | 0 | 6/10 (60) | 5/10 (50) | 45 |
| Ex. 10 | 30/30 | 0 | A | 110 | 0 | 4/10 (40) | 4/10 (40) | 56 |
| Ex. 11 | 60/30 | 0 | B | 110 | 95 | 7/10 (70) | 5/10 (50) | 35 |

Notes:
[1]A: The immobilization method using N-hydroxysuccinimide (active ester method).
B: The immobilization method using 1-ethyl-3-(3-dimethylaminopropyl)carbodiimide (WSC method).

Example 12 (Reference)

A quantity of paraffin was impregnated to a depth of about 50 μm from the outer surface of an EPTFE tube having an inner diameter of 2 mm, an outer diameter of 3 mm, a length of 20 cm, a fibril length of 30 μm and a porosity of 75%. Then, the tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid, ungrafted polymer of acrylic acid and paraffin were washed off, and an acrylic acid-grafted EPTFE tube was obtained. The grafted amount of acrylic acid was about 235 μg per 1 cm of the tube when calculated from the weight change of the tubes.

Example 13 (Reference)

A quantity of paraffin was impregnated to a depth of about 100 μm from the outer surface of an EPTFE tube having an inner diameter of 2 mm, an outer diameter of 3 mm, a length of 20 cm, a fibril length of 30 μm and a porosity of 75%. Then, the tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid, ungrafted polymer of acrylic acid and paraffin were washed off, and an acrylic acid-grafted EPTFE tube was obtained. The grafted amount of acrylic acid was about 195 μg per 1 cm of the tube when calculated from the weight change of the tubes.

Example 14 (Reference)

A quantity of paraffin was impregnated to a depth of about 300 μm from the outer surface of an EPTFE tube having an inner diameter of 2 mm, an outer diameter of 3 mm, a length of 20 cm, a fibril length of 30 μm and a porosity of 75%. Then, the tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid, ungrafted polymer of acrylic acid and paraffin were washed off, and an acrylic acid-grafted EPTFE tube was obtained. The grafted amount of acrylic acid was about 90 μg per 1 cm of the tube when calculated from the weight change of the tubes.

Example 15 (Reference)

A quantity of paraffin was impregnated to a depth of about 480 μm from the outer surface of an EPTFE tube having an inner diameter of 2 mm, an outer diameter of 3 mm, a length of 20 cm, a fibril length of 30 μm and a porosity of 75%. Then, the tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid, ungrafted polymer of acrylic acid and paraffin were washed off, and an acrylic acid-grafted EPTFE tube was obtained. The grafted amount of acrylic acid was about 20 μg per 1 cm of the tube when calculated from the weight change of the tubes.

Example 16

The acrylic acid-grafted EPTFE tube produced in Example 14 was dipped in a 0.05% aqueous solution of heparin (available from SANOFI) for 10 minutes and freeze dried, and the heparin-immobilized EPTFE tube was obtained. The immobilized amount of heparin was about 550 μg per 1 cm of the tube when calculated from the weight change.

Example 17

The acrylic acid-grafted EPTFE tube prepared in Example 14 was dipped in an aqueous solution containing 0.05% of fibronectin (derived from bovine plasma, manufactured by NIPPON HAM) and 0.5% of 1-ethyl-3-(3-dimethylaminopropyl)carbodiimide, pH of which had been adjusted to 5 with 1N hydrochloric acid, for 24 hours and washed with water, and the fibronectin-immobilized EPTFE tube was obtained. The immobilized amount of fibronectin was about 160 μg per 1 cm of the tube.

Example 18

The fibronectin-immobilized EPTFE tube prepared in Example 17 was dipped in a 0.5% aqueous solution of heparin (available from SANOFI) for 10 minutes and freeze dried, and the heparin-immobilized EPTFE tube was obtained. The immobilized amount of heparin was about 550 μg 1 cm of the tube when calculated from the weight change.

Comparative Example 4

An EPTFE tube having an inner diameter of 2 mm, an outer diameter of 3 mm, a length of 20 cm, a fibril length of 30 μm and a porosity of 75% was used as an artificial blood vessel without any treatment.

Comparative Example 5

An EPTFE tube having an inner diameter of 2 mm, an outer diameter of 3 mm, a length of 20 cm, a fibril length of 30 μm and a porosity of 75% was dipped in a mixture of a

TABLE 2

| Ex. No. | Thickness of hydrophilic layer from inner surface (μm) (% based on wall thickness) | Immobilized amount of methacrylic acid (μg/cm) | Immobilized amount of heparin (μg/cm) | Immobilized amount of fibronectin (μg/cm) | Patency ratio (%) after | | Water absorption[1] |
|---|---|---|---|---|---|---|---|
| | | | | | One week | oOe month | |
| Ex. 12 | 450 (90) | 235 | 0 | 0 | 7/10 (70) | 6/10 (60) | 93 |
| Ex. 13 | 400 (80) | 195 | 0 | 0 | 8/10 (80) | 6/10 (60) | 82 |
| Ex. 14 | 200 (40) | 90 | 0 | 0 | 9/10 (90) | 7/10 (70) | 45 |
| Ex. 15 | 20 (4) | 20 | 0 | 0 | 8/10 (80) | 5/10 (50) | 5 |
| Ex. 16 | 200 (40) | 90 | 550 | 0 | 10/10 (100) | 7/10 (70) | 45 |
| Ex. 17 | 200 (40) | 90 | 0 | 160 | 8/10 (80) | 8/10 (80) | 45 |
| Ex. 18 | 200 (40) | 90 | 550 | 160 | 10/10 (100) | 10/10 (100) | 44 |
| C. Ex. 4 | 0 (0) | 0 | 0 | 0 | 6/10 (60) | 3/10 (30) | 0 |
| C. Ex. 5 | 500 (100) | 250 | 0 | 0 | 4/10 (40) | 2/10 (20) | 100 |
| C. Ex. 6 | 500 (100) | 250 | 920 | 0 | 2/10 (20) | 0/10 (0) | 100 |
| C. Ex. 7 | 480 (96) | 250 | 0 | 0 | 4/10 (40) | 3/10 (30) | 98 |

Notes:
[1]The water absorption was calculated from the weight change after dipping the tube in water for 5 seconds with those in Comparative Examples 5 and 6 being 100.

1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid and ungrafted polymer of acrylic acid were washed off, and an acrylic acid-grafted EPTFE tube was obtained. The grafted amount of acrylic acid was about 250 μg per 1 cm of the tube when calculated from the weight change of the tubes.

Comparative Example 6

The acrylic acid-grafter EPTFE tube prepared in the same manner as Comparative Example 5 was dipped in a 0.5% aqueous solution of heparin (available from SANOFI) for 10 minutes and freeze dried, and the heparin-immobilized EPTFE tube was obtained. The immobilized amount of heparin was about 920 μg 1 cm of the tube when calculated from the weight change.

Comparative Example 7

A quantity of paraffin was impregnated to a depth of about 20 μm from the outer surface of an EPTFE tube having an inner diameter of 2 mm, an outer diameter of 3 mm, a length of 20 cm, a fibril length of 30 μm and a porosity of 75%. Then, the tube was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of acrylic acid (1 g) in water (20 ml) was added and reacted at 80° C. for 10 hours. After this, excessive acrylic acid, ungrafted polymer of acrylic acid and paraffin were washed off, and an acrylic acid-grafted EPTFE tube was obtained. The grafted amount of acrylic acid was about 250 μg per 1 cm of the tube when calculated from the weight change of the tubes.

The patency ratios of the artificial blood vessels produced in Examples 12–18 and Comparative Examples 4–7 were evaluated in the same way as in Examples 1–11. The results are shown in Table 2.

Example 19

An EPTFE tube having an inner diameter of 4 mm, an outer diameter of 5 mm and a length of 30 mm was dipped in a mixture of a 1.4 M solution of methyllithium in ethyl ether (20 ml) and hexamethylphosphoric amide (2 ml) at 0° C. in a nitrogen atmosphere for 30 minutes. After discarding the mixture, a solution of methacrylic acid (3 g) in tetrahydrofuran (20 ml) was added and reacted at 60° C. for 10 hours. After this, excessive methacrylic acid and ungrafted polymer of methacrylic acid were washed off, and a methacrylic acid-grafted EPTFE tube was obtained. The grafted amount of methacrylic acid was about 132 μg per 1 cm of the tube when calculated from the weight change of the tube.

Polyallylamine having an acetylation rate of 0 mole % was reacted with the obtained methacrylic acid-grafted EPTFE tube in the presence of 1-ethyl-3-(dimethylaminopropyl)carbodiimide, and immobilized to the tube through the covalent bond. The immobilized amount of polyallylamine was about 162 μg/cm when calculated from the weight change of the tube.

The tube was dipped in a 10% aqueous solution of heparin for 2 hours for ionically bonding heparin to the tube, and the heparin-immobilized EPTFE tube was obtained. The immobilized amount of heparin was about 62 UNIT per 1 cm of the tube.

The sustained releasability of heparin from the obtained heparin-immobilized EPTFE tube was evaluated in vitro.

A 2 M (mol/l) aqueous solution of sodium chloride was flowed through the heparin-immobilized EPTFE tube at a flow rate of 10 ml/min. with a peristaltic pump, and a remaining amount of heparin was measured after a specific period. The results are shown in FIG. 1.

Ten heparin-immobilized EPTFE artificial blood vessels were implanted in carotid arteries of ten dogs, and a patency ratio after one and four weeks was checked. The results are shown in Table 3.

Example 20

Methacrylic acid was graft polymerized on the EPTFE tube in an amount of 132 μg/cm in the same manner as in Example 19. Then, polyallylamine having an acetylation rate of 30 mole % was immobilized through covalent bond in an amount of 152 μg/cm, and further heparin was immobilized through ion bond in an amount of 56 UNIT/cm in the same manners as in Example 19.

The sustained releasability of heparin from the obtained heparin-immobilized EPTFE tube was evaluated in vitro in the same method as in Example 19. The results are shown in FIG. 1.

Ten heparin-immobilized EPTFE artificial blood vessels were implanted in carotid arteries of ten dogs, and a patency ratio after one and four weeks was checked. The results are shown in Table 3.

Example 21

Methacrylic acid was graft polymerized on the EPTFE tube in an amount of 132 μg/cm in the same manner as in Example 19. Then, polyallylamine having an acetylation rate of 60 mole % was immobilized through covalent bond in an amount of 138 μg/cm, and further heparin was immobilized through ion bond in an amount of 48 UNIT/cm in the same manners as in Example 19.

The sustained releasability of heparin from the obtained heparin-immobilized EPTFE tube was evaluated in vitro in the same method as in Example 19. The results are shown in FIG. 1.

Ten heparin-immobilized EPTFE artificial blood vessels were implanted in carotid arteries of ten dogs, and a patency ratio after one and four weeks was checked. The results are shown in Table 3.

Example 22

Methacrylic acid was graft polymerized on the EPTFE tube in an amount of 232 μg/cm in the same manner as in Example 19 except that 6 g of methacrylic acid was used. Then, polyallylamine having an acetylation rate of 0 mole % was immobilized through covalent bond in an amount of 353 μg/cm, and further heparin was immobilized through ion bond in an amount of 105 UNIT/cm in the same manners as in Example 19.

The sustained releasability of heparin from the obtained heparin-immobilized EPTFE tube was evaluated in vitro in the same method as in Example 19. The results are shown in FIG. 1.

Ten heparin-immobilized EPTFE artificial blood vessels were implanted in carotid arteries of ten dogs, and a patency ratio after one and four weeks was checked. The results are shown in Table 3.

Example 23

Methacrylic acid was graft polymerized on the EPTFE tube in an amount of 232 μg/cm in the same manner as in Example 19 except that 6 g of methacrylic acid was used. Then, polyallylamine having an acetylation rate of 30 mole % was immobilized through covalent bond in an amount of 348 μg/cm, and further heparin was immobilized through ion bond in an amount of 96 UNIT/cm in the same manners as in Example 19.

The sustained releasability of heparin from the obtained heparin-immobilized EPTFE tube was evaluated in vitro in the same method as in Example 19. The results are shown in FIG. 1.

Ten heparin-immobilized EPTFE artificial blood vessels were implanted in carotid arteries of ten dogs, and a patency ratio after one and four weeks was checked. The results are shown in Table 3.

Example 24

Methacrylic acid was graft polymerized on the EPTFE tube in an amount of 232 μg/cm in the same manner as in Example 19 except that 6 g of methacrylic acid was used. Then, polyallylamine having an acetylation rate of 60 mole % was immobilized through covalent bond in an amount of 339 μg/cm, and further heparin was immobilized through ion bond in an amount of 88 UNIT/cm in the same manners as in Example 19.

The sustained releasability of heparin from the obtained heparin-immobilized EPTFE tube was evaluated in vitro in the same method as in Example 19. The results are shown in FIG. 1.

Ten heparin-immobilized EPTFE artificial blood vessels were implanted in carotid arteries of ten dogs, and a patency ratio after one and four weeks was checked. The results are shown in Table 3.

Comparative Example 8

An EPTFE tube having an inner diameter of 4 mm, an outer diameter of 5 mm and a length of 30 mm was dipped successively in ethanol, and water and maintained in a 0.1% solution of protamine for one hour. After this, the tube was dipped in a 1% aqueous solution of glutaraldehyde.

The tube was dipped in a 10% aqueous solution of heparin for 2 hours for ionically bonding heparin to the tube, and the heparin-immobilized EPTFE tube was obtained.

The ungrafted polymer of meth of protamine and heparin were about 120 μg/cm and 31 UNIT/cm, respectively.

The sustained releasability of heparin from the obtained heparin-immobilized EPTFE tube was evaluated in vitro in the same method as in Example 19. The results are shown in FIG. 2.

Ten heparin-immobilized EPTFE artificial blood vessels were implanted in carotid arteries of ten dogs, and a patency ratio after one and four weeks was checked. The results are shown in Table 3.

Comparative Example 9

An EPTFE tube having an inner diameter of 4 mm, an outer diameter of 5 mm and a length of 30 mm was dipped successively in ethanol, water and then a 0.2% solution of protamine for one hour. After this, the tube was dipped in a 1% aqueous solution of glutaraldehyde.

The tube was dipped in a 10% aqueous solution of heparin for 2 hours for ionically bonding heparin to the tube, and the heparin-immobilized EPTFE tube was obtained.

The ungrafted polymer of meth of protamine and heparin were about 220 μg/cm and 51 UNIT/cm, respectively.

The sustained releasability of heparin from the obtained heparin-immobilized EPTFE tube was evaluated in vitro in the same method as in Example 19. The results are shown in FIG. 2.

Ten heparin-immobilized EPTFE artificial blood vessels were implanted in carotid arteries of ten dogs, and a patency ratio after one and four weeks was checked. The results are shown in Table 3.

Comparative Example 10

An EPTFE tube having an inner diameter of 4 mm, an outer diameter of 5 mm and a length of 30 mm was dipped successively in ethanol, water and then a 0.3% solution of protamine for one hour. After this, the tube was dipped in a 1% aqueous solution of glutaraldehyde.

The tube was dipped in a 10% aqueous solution of heparin for 2 hours for ionically bonding heparin to the tube, and the heparin-immobilized EPTFE tube was obtained.

The amounts of the immobilized protamine and heparin were about 320 μg/cm and 53 UNIT/cm, respectively.

The sustained releasability of heparin from the obtained heparin-immobilized EPTFE tube was evaluated in vitro in the same method as in Example 19. The results are shown in FIG. 2.

Ten heparin-immobilized EPTFE artificial blood vessels were implanted in carotid arteries of ten dogs, and a patency ratio after one and four weeks was checked. The results are shown in Table 3.

TABLE 3

| Ex. No. | Patency ratio after | |
| --- | --- | --- |
|  | One week | One month |
| Ex. 19 | 6/10 | 6/10 |
| Ex. 20 | 7/10 | 7/10 |
| Ex. 21 | 10/10 | 7/10 |
| Ex. 22 | 7/10 | 7/10 |
| Ex. 23 | 10/10 | 10/10 |
| Ex. 24 | 10/10 | 9/10 |
| C. Ex. 8 | 6/10 | 3/10 |
| C. Ex. 9 | 7/10 | 3/10 |
| C. Ex. 10 | 7/10 | 3/10 |

Example 25

An EPTFE tube having an inner diameter of 4 mm, an outer diameter of 5 mm and a length of 1 m was dipped in a mixture of a 1.4 M solution of methyllithium in ethyl ether (20 ml) and hexamethylphosphoric amide (2 ml) at 0° C. in a nitrogen atmosphere for 30 minutes. After discarding the mixture, a solution of methacrylic acid (5 g) in tetrahydrofuran (20 ml) was added and reacted at 60° C. for 10 hours. After this, excessive methacrylic acid and ungrafted polymer of methacrylic acid were washed off, and a methacrylic acid-grafted EPTFE tube was obtained. The grafted amount of methacrylic acid was about 182 μg per 1 cm of the tube when calculated from the weight change of the tube.

Next, the methacrylic acid-grafted EPTFE tube was dipped in a solution of N-hydroxysuccinimide (2.1 g) and dicyclohexylcarbodiimide (1.9 g) in 1,4-dioxane (100 ml) at 0° C. for 12 hours, and acrylic acid was changed to the N-hydroxysuccinimide ester.

The esterified tube was dipped in a solution of fibronectin (30 mg) and transferrin (30 mg) in a phosphate buffer (pH of 11) (100 ml), and fibronectin and transferrin were immobilized through covalent bond to the ester groups. The ungrafted polymer of meth of fibronectin and transferrin were about 122 μg and 95 μg per 1 cm of the tube, respectively.

Ten artificial blood vessels (each 3 cm in length) was implanted in carotid arteries of ten dogs. A patency ratio was 8/10 (80%) and a ratio of the surface area covered with endothelial cells was 95% after four weeks.

Example 26

Fibronectin and insulin were immobilized onto the EPTFE tube in amounts of 132 μg/cm and 102 μg/cm, respectively in the same manner as in Example 25 except that insulin was used in place of transferrin.

Ten artificial blood vessels was implanted in carotid arteries of ten dogs. A patency ratio was 9/10 (90%) and a ratio of the surface area covered with endothelial cells was 92% after four weeks.

Example 27

Fibronectin and TGF-α were immobilized onto the EPTFE tube in amounts of 118 μg/cm and 89 μg/cm, respectively in the same manner as in Example 25 except that TGF-α was used in place of transferrin.

Ten artificial blood vessels was implanted in carotid arteries of ten dogs. A patency ratio was 8/10 (80%) and a ratio of the surface area covered with endothelial cells was 95% after four weeks.

Example 28

Fibronectin and FGF were immobilized onto the EPTFE tube in amounts of 120 μg/cm and 90 μg/cm, respectively in the same manner as in Example 25 except that FGF was used in place of transferrin.

Ten artificial blood vessels was implanted in carotid arteries of ten dogs. A patency ratio was 9/10 (90%) and a ratio of the surface area covered with endothelial cells was 89% after four weeks.

Example 29

2-Hydroxyethyl methacrylate was graft polymerized on the EPTFE tube in an amount of 246 μg/cm in the same manner as in Example 25 except that 2-hydroxyethyl methacrylate was used in place of methacrylic acid. Then, the EPTFE tube was dipped in solution of 2,2,2-trifluoromethanesulfonyl chloride in dichloromethane for forming 2,2,2-trifluoromethanesulfonate ester.

The esterified tube was dipped in a solution of fibronectin (30 mg) and transferrin (30 mg) in a phosphate buffer (pH of 11) (100 ml), and fibronectin and transferrin were immobilized through covalent bond in amounts of 128 μg and 89 μg per 1 cm of the tube, respectively.

Ten artificial blood vessels was implanted in carotid arteries of ten dogs. A patency ratio was 8/10 (80%) and a ratio of the surface area covered with endothelial cells was 95% after four weeks.

Example 30

Methacrylic acid was graft polymerized on the EPTFE tube in an amount of 185 μg/cm in the same manner as in Example 25. Then, the tube was dipped in a solution of fibronectin (30 mg) and transferrin (30 mg) in a phosphate buffer (100 ml) at pH of 1.5 for 12 hours in the presence of 1-ethyl-3-(3-dimethylaminopropyl)-carbodiimide (30 mg), and fibronectin and transferrin were immobilized through covalent bond in amounts of 120 μg and 108 μg per 1 cm of the tube, respectively.

Ten artificial blood vessels was implanted in carotid arteries of ten dogs. A patency ratio was 6/10 (60%) and a ratio of the surface area covered with endothelial cells was 50% after four weeks.

Example 31

Methacrylic acid was graft polymerized on the EPTFE tube in an amount of 178 μg/cm in the same manner as in Example 25. Next, the methacrylic acid-grafted EPTFE tube was dipped in a solution of N-hydroxysuccinimide (2.1 g) and dicyclohexylcarbodiimide (1.9 g) in 1,4-dioxane (100 ml) at 0° C. for 12 hours, and methacrylic acid was changed to the N-hydroxysuccinimide ester.

The esterified tube was dipped in a solution of fibronectin (30 mg) in a phosphate buffer (pH of 11) (100 ml), and fibronectin was immobilized through covalent bond to the ester groups. The immobilized amount of fibronectin was about 122 μg per 1 cm of the tube.

Ten artificial blood vessels was implanted in carotid arteries of ten dogs. A patency ratio was 3/10 (30%) and a ratio of the surface area covered with endothelial cells was 70% after four weeks.

Example 32

Transferrin was immobilized to the esterified tube through the covalent bond in an amount of 108 μg/cm in the same manner as in Example 30 except that transferrin alone was used.

Ten artificial blood vessels was implanted in carotid arteries of ten dogs. A patency ratio was 3/10 (30%) and a ratio of the surface area covered with endothelial cells was 70% after four weeks.

Comparative Example 11

The same EPTFE tube as used in Example 25 was dipped in an aqueous solution of fibronectin (30 mg) and transferrin (30 mg) for coating fibronectin and transferrin in amounts of 89 μg/cm and 102 μg/cm, respectively, followed by dipping in a 1% aqueous solution of glutaraldehyde for crosslinking them.

Ten artificial blood vessels was implanted in carotid arteries of ten dogs. A patency ratio was 2/10 (20%) and a ratio of the surface area covered with endothelial cells was 40% after four weeks.

Example 33

An EPTFE tube having an inner diameter of 4 mm, an outer diameter of 5 mm and a fibril length of 30 μm was dipped in a mixture of a 1.4 M solution of methyllithium in ethyl ether (20 ml) and hexamethylphosphoric amide (2 ml) at −10° C. in an argon atmosphere for 30 minutes. After discarding the mixture, a solution of methacrylic acid (5 g) in water (20 ml) was added and reacted at 80° C. for 10 hours. After this, excessive methacrylic acid and ungrafted polymer of methacrylic acid were washed off, and a methacrylic acid-grafted EPTFE tube was obtained. The grafted amount of methacrylic acid was about 220 μg per 1 cm of the tube when calculated from the weight change of the tubes.

The tube was dipped in a solution of N-hydroxysuccinimide (2.1 g) and dicyclohexylcarbodiimide (1.9 g) in 1,4-dioxane (100 ml) at 0° C. for 12 hours, and methacrylic acid was changed to the N-hydroxysuccinimide ester. The esterified tube was dipped in a solution of fibronectin (30 mg) in a phosphate buffer (pH of 11) (100 ml), and fibronectin was immobilized through covalent bond to the ester groups. The immobilized amount of fibronectin was about 205 μg per 1 cm of the tube when calculated from the weight change.

Next, the tube was compressed in the expanded direction, that is, the longitudinal direction of the tube, and fibrils between the nodes were warped so that only the nodes were exposed to the bore of the tube. Then, a 5% solution of polyallylamine (molecular weight of about 100,000) in phosphate buffer (pH=11) flowed through the bore of the tube for 12 hours while maintaining the compressed state of the tube, and polyallylamine was immobilized onto the nodes appearing on the inner wall surface of the tube through covalent bond. During this treatment, the polyallylamine solution did not exude onto the outside surface of the tube.

After this, a 5% aqueous solution of heparin (available from SANOFI) flowed through the bore of the tube for 1 hour while maintaining the compressed state of the tube. Then, the tube was freed from compression and washed with water, followed by freeze drying. The immobilized amount of heparin was 17 UNIT/cm.

Only the nodes of the EPTFE were dyed when the tube was dipped in a methylene blue solution. This indicated that heparin was immobilized to these nodes.

Example 34

An EPTFE tube having an inner diameter of 4 mm, an outer diameter of 5 mm and a fibril length of 60 μm was treated with methyllithium and then methacrylic acid was graft polymerized on the EPTFE tube in the same manners as in Example 33. The grafted amount of methacrylic acid was about 195 μg per 1 cm of the tube.

The methacrylic acid-grafted EPTFE tube was treated with N-hydroxysuccinimide and then fibronectin in the same manners as in Example 33. The immobilized amount of fibronectin was 198 μg/cm.

Next, the fibronectin-immobilized EPTFE tube was treated with polyallylamine and then heparin in the same manners as in Example 33. The immobilized amount of heparin was 14 UNIT/cm, and heparin was immobilized only on the nodes which appeared on the inner surface of the tube.

Example 35

An EPTFE tube, which had an inner diameter of 4 mm, an outer diameter of 5 mm and a fibril length of 60 μm in a thickness of 250 μm from the inner surface of the tube and a fibril length of 30 μm in other part of the tube, was treated with methyllithium and then methacrylic acid was graft polymerized on the EPTFE tube in the same manners as in Example 33. The grafted amount of methacrylic acid was about 231 μg per 1 cm of the tube.

The methacrylic acid-grafted EPTFE tube was treated with N-hydroxysuccinimide and then fibronectin in the same manners as in Example 33. The immobilized amount of fibronectin was 211 μg/cm.

Next, the fibronectin-immobilized EPTFE tube was treated with polyallylamine and then heparin in the same manners as in Example 33. The immobilized amount of heparin was 16 UNIT/cm, and heparin was immobilized only on the nodes which appeared on the inner surface of the tube.

Example 36

The methacrylic acid-grafted EPTFE tube produced in the same manner as in Example 35 was treated with N-hydroxysuccinimide in the same manner as in Example 33, and then dipped in a solution of fibronectin (15 mg) and transferrin (15 mg) in phosphate buffer (pH=11) (100 ml). The immobilized amounts of fibronectin and transferrin were 121 μg/cm and 118 μg/cm, respectively.

Next, the fibronectin/transferrin-immobilized EPTFE tube was treated with polyallylamine and then heparin in the same manners as in Example 33. The immobilized amount of heparin was 16 UNIT/cm, and heparin was immobilized only on the nodes which appeared on the inner surface of the tube.

Example 37

The methacrylic acid-grafted EPTFE tube produced in the same manner as in Example 35 was dipped in a solution of 1-ethyl-3-(3-dimethylaminopropyl)carbodiimide (30 mg), fibronectin (15 mg) and transferrin (15 mg) in distilled water (100 ml), pH of which was adjusted to 5 with 1N hydrochloric acid, for 24 hours. The immobilized amounts of fibronectin and transferrin were 131 μg/cm and 120 μg/cm, respectively.

Next, the fibronectin/transferrin-immobilized EPTFE tube was treated with polyallylamine and then heparin in the same manners as in Example 33. The immobilized amount of heparin was 16 UNIT/cm, and heparin was immobilized only on the nodes which appeared on the inner surface of the tube.

Comparative Example 12

An EPTFE tube having an inner diameter of 4 mm, an outer diameter of 5 mm and a fibril length of 30 μm was used as an artificial blood vessel.

Example 38

The methacrylic acid-grafted EPTFE tube prepared in the same manner as in Example 33 was treated with N-hydroxysuccinimide and then fibronectin in the same manners as in Example 33. The immobilized amount of fibronectin was 192 μg/cm.

Next, the fibronectin-immobilized EPTFE tube in the uncompressed state was dipped in a 5% solution of polyallylamine in phosphate buffer (pH=11) for 12 hours, and polyallylamine was immobilized on the inner and outer surfaces and also the pore surfaces of the tube. Then, the tube was dipped in a 10% aqueous solution of heparin (available from SANOFI) for 1 hour and washed with water, followed by freeze drying. The immobilized amount of heparin was 85 UNIT/cm, and heparin was immobilized on all the surfaces of the tube, that is, the inner and outer surfaces and pore surfaces of the tube.

Example 39

The methacrylic acid-grafted EPTFE tube prepared in the same manner as in Example 33 was treated with N-hydroxysuccinimide in the same manner as in Example 33, and then dipped in a solution of fibronectin (15 mg) and transferrin (15 mg) in phosphate buffer (pH=11) (100 ml). The immobilized amounts of fibronectin and transferrin were 118 μg/cm and 109 μg/cm, respectively.

Next, the fibronectin/transferrin-immobilized EPTFE tube in the uncompressed state was dipped in a 5% solution of polyallylamine in phosphate buffer (pH=11) for 12 hours, and polyallylamine was immobilized on the inner and outer surfaces and also the pore surfaces of the tube. Then, the tube was dipped in a 10% aqueous solution of heparin (available from SANOFI) for 1 hour and washed with water followed by freeze drying. The immobilized amount of heparin was 83 UNIT/cm, and heparin was immobilized on all the surfaces of the tube, that is, the inner and outer surfaces and pore surfaces of the tube.

Example 40

An EPTFE tube having an inner diameter of 4 mm, an outer diameter of 5 mm and a fibril length of 30 μm was treated with methyllithium and then methacrylic acid was graft polymerized on the EPTFE tube in the same manners as in Example 33 except that the amount of methacrylic acid was changed from 5 g to 3 g. The grafted amount of methacrylic acid was about 220 μg per 1 cm of the tube when calculated from the weight change.

The methacrylic acid-grafted EPTFE tube was treated with N-hydroxysuccinimide and then fibronectin in the same manners as in Example 33. The immobilized amount of fibronectin was 192 μg/cm.

Comparative Example 13

An EPTFE tube, which had an inner diameter of 4 mm, an outer diameter of 5 mm and a fibril length of 60 μm in a thickness of 250 μm from the inner wall surface of the tube and a fibril length of 30 μm in other part of the tube, was used as an artificial blood vessel.

Ten artificial blood vessels (each having an inner diameter of 4 mm and a length of 4 cm) produced in each of Examples 33 to 40 and Comparative Examples 12 and 13 were implanted in carotid arteries of ten dogs. A patency ratio after one week and one month was checked, and a ratio of the surface area covered with endothelial cells was evaluated. The results are shown in Table 4.

TABLE 4

| Ex. No. | Fibril length in inner layer/ outer layer (μm/μm) | Immobilization of tissue-inducing material | | | | Heparin-Immobilization | | | | Covering ratio of endo-thelial cell (%) |
|---|---|---|---|---|---|---|---|---|---|---|
| | | Method[1] | Fibro-nectin (μg/cm) | Trans-ferrin (μg/cm) | Immobilized part | Immobi-lized amount (UNIT/cm) | Patency ratio (%) after | | | |
| | | | | | | | one week | one month | | |
| Ex. 33 | 30/30 | A | 205 | 0 | Nodes on inner surface | 17 | 10/10 | 8/10 | 58 | |
| Ex. 34 | 60/60 | A | 198 | 0 | Nodes on inner surface | 14 | 10/10 | 9/10 | 63 | |
| Ex. 35 | 60/30 | A | 211 | 0 | Nodes on inner surface | 16 | 10/10 | 10/10 | 68 | |
| Ex. 36 | 60/30 | A | 121 | 118 | Nodes on inner surface | 16 | 10/10 | 10/10 | 85 | |
| Ex. 37 | 60/30 | B | 131 | 120 | Nodes on inner surface | 16 | 10/10 | 9/10 | 78 | |
| C. Ex. 12 | 30/30 | — | 0 | 0 | — | 0 | 5/10 | 4/10 | 24 | |
| Ex. 38 | 30/30 | A | 192 | 0 | All surfaces | 85 | 6/10 | 6/10 | 31 | |

TABLE 4-continued

| Ex. No. | Fibril length in inner layer/ outer layer (μm/μm) | Immobilization of tissue-inducing material | | | | Heparin-Immobilization | | | Covering ratio of endo-thelial cell (%) |
|---|---|---|---|---|---|---|---|---|---|
| | | Method[1] | Fibro-nectin (μg/cm) | Trans-ferrin (μg/cm) | Immobilized part | Immobi-lized amount (UNIT/cm) | Patency ratio (%) after | | |
| | | | | | | | one week | one month | |
| Ex. 39 | 30/30 | A | 118 | 109 | All surfaces | 83 | 7/10 | 5/10 | 36 |
| Ex. 40 | 30/30 | A | 192 | 0 | — | 0 | 4/10 | 3/10 | 48 |
| C. Ex. 13 | 60/30 | — | 0 | 0 | — | 0 | 6/10 | 5/10 | 28 |

Notes:
[1]A: The immobilization method using N-hydroxysuccinimide (active ester method).
B: The immobilization method using 1-ethyl-3-(3-dimethylaminopropyl)carbodiimide (WSC method).

What is claimed is:

1. An artificial blood vessel comprising:
   a tube formed from expanded polytetrafluoroethylene comprising fibrils and nodes connecting fibrils,
   wherein said tube has an inner surface and an outer surface,
   in which the inner surface of said tube and surfaces of fibrils and nodes comprise a hydrophilic layer extending to a depth of between 5% and 96% of the wall thickness of said tube in a radial direction from the inner surface toward the outer surface of said tube, and
   a tissue-inducing substance which is immobilized on said inner surface and said surfaces of fibrils and nodes of the hydrophilic layer.

2. An artificial blood vessel according to claim 1, which further comprises an anti-thrombotic substance immobilized on at least a part of a surface of said tube which will be in contact with blood in use.

3. An artificial blood vessel according to claim 1 or 2, wherein a mean fibril length of said expanded polytetrafluoroethylene on a side which will be in contact with blood in use is at least 60 μm.

4. An artificial blood vessel according to claim 1 or 2, wherein a mean fibril length of said expanded polytetrafluoroethylene on a side which will be in contact with the blood in use is at least 60 μm, and said tube comprises at least one layer in which a mean fibril length of said expanded polytetrafluoroethylene is 40 μm or less.

5. An artificial blood vessel according to claim 1, wherein said tissue-inducing substance is at least one material selected from the group consisting of a cell-adhesion material and a cell-growth material.

6. An artificial blood vessel according to claim 5, wherein said cell-adhesion material is fibronectin.

7. An artificial blood vessel according to claim 5, wherein said cell-growth material is at least one material selected from the group consisting of TGF-α, transferrin, insulin and fibroblast growth factor.

8. An artificial blood vessel according to claim 2, wherein said anti-thrombotic substance is heparin.

9. An artificial blood vessel according to claim 2, wherein said anti-thrombotic substance is ionically immobilized to a polyamine or its salt which is covalently bonded through a polymer which has been graft polymerized on said surface of said tube which will be in contact with blood in use.

10. An artificial blood vessel according to claim 9, wherein said polyamine is at least one polyamine selected from the group consisting of polyallylamine, polyvinylamine and polyethylene imine.

11. An artificial blood vessel according to claim 9, wherein said polyamine has a molecular weight of between 1000 and 100,000, and 0 to 90 mole % of the amino groups of said polyamine are acetylated.

12. An artificial blood vessel according to claim 1, wherein an anti-thrombotic substance is immobilized on nodes in a part of a surface of said tube which will be in contact with the blood in use.

13. An artificial blood vessel according to claim 1, wherein said tissue-inducing substance is immobilized through covalent bond on said inner surface and said surfaces of fibrils and nodes by reacting said tissue-inducing substance with an ester of a carboxylic acid or a sulfonate ester of a hydroxyl group which has been formed on said inner surface and said surfaces of fibrils and nodes by graft polymerization.

14. An artificial blood vessel comprising:
   a tube formed from expanded polytetrafluoroethylene comprising fibrils and nodes connecting fibrils,
   wherein said tube has an inner surface and an outer surface,
   in which the inner surface of said tube and surfaces of fibrils and nodes comprises a hydrophilic layer extending to a depth of between 5% and 96% of the wall thickness of said tube in a radial direction from the inner surface towards the outer surface of said tube, and
   at least one material selected from the group consisting of a tissue-inducing substance and an anti-thrombotic substance, which is immobilized on said inner surface and said surfaces of fibrils and nodes of hydrophilic layer.

* * * * *